US005455221A

United States Patent [19]

Cutler et al.

[11] Patent Number: 5,455,221

[45] Date of Patent: Oct. 3, 1995

[54] BOTCINOLIDE: A NATURAL PRODUCT HERBICIDE WHICH IS A HYDROXYLATED MONALACTONE

[75] Inventors: Horace G. Cutler, Watkinsville, Ga.; John M. Jacyno, Ada, Ohio

[73] Assignee: The United States of America as represented by the Secretary of Agriculture, Washington, D.C.

[21] Appl. No.: 235,432

[22] Filed: Apr. 29, 1994

[51] Int. Cl.$^6$ .................................................. C07D 313/00

[52] U.S. Cl. ............................................ 504/291; 549/271

[58] Field of Search ........................ 504/291; 435/254.1; 424/93 Q; 549/271

OTHER PUBLICATIONS

Goodman et al., Protoplasma 166(1–2): 107–109 (1992).
Williamson et al., New Phytol. 111(1): 81–88 (1989).
El–Dein et al., Acta Phytopathol Acad. Sci Hung 20(1–2): 163–174 (1985).
Abstract, Proceedings, Nineteenth Annual Meeting, Plant Growth Regulator Society of America, San Francisco, Calif., Jul. 17–20, 1992, "Isolation of a New Biologically–Active Metabolite from *Botrytis Cinerea*", H. G. Cutler, et al., published May 1993.
Cutler, Horace G., et al. "Botcinolide: A Biologically Active Natural Product from *Botrytis cinerea*", Biosci. Biotech. Biochem., 11, vol. 57, pp. 1980–1982, Nov. 1993.

*Primary Examiner*—Marian C. Knode
*Assistant Examiner*—Jean C. Witz
*Attorney, Agent, or Firm*—M. Howard Silverstein; Randall E. Deck; John D. Fado

[57] ABSTRACT

A novel organic compound, designated botcinolide, has been isolated which possesses significant phytotoxic activity and which may be used as a biodegradable contact herbicide. The compound is a hydroxylated nonalactone that is esterified with 4-hydroxy-2-octenoic acid, and has the following structure:

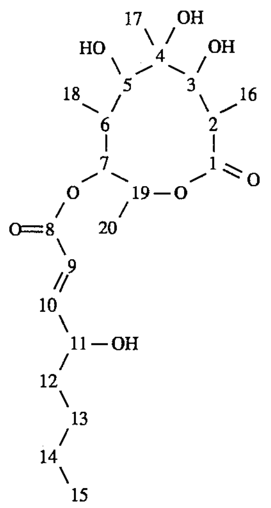

Botcinolide is produced by culture of a novel strain of the fungus *Botrytis cinerea*, designated UK 185, and may be subsequently recovered from the culture medium and purified.

4 Claims, No Drawings

BOTCINOLIDE: A NATURAL PRODUCT HERBICIDE WHICH IS A HYDROXYLATED MONALACTONE

BACKGROUND OF THE INVENTION

This invention relates to a novel hydroxylated nonalactone compound produced by a strain of the fungus *Botrytis cinerea,* and its use as a herbicide.

*Botrytis cinerea* is a common soil fungus which is the causative agent of grey mold rot, one of the most widespread fungal diseases affecting a variety of plants, including agronomically important fruits and vegetables such as lettuce, tomatoes, strawberries, raspberries and grapes.

SUMMARY OF THE INVENTION

We have discovered a novel organic compound possessing significant phytotoxic activity and which may be used as a biodegradable contact herbicide. The compound, which has been given the name botcinolide, is a hydroxylated nonalactone that is esterified with 4-hydroxy-2-octenoic acid, and has the following structure (I):

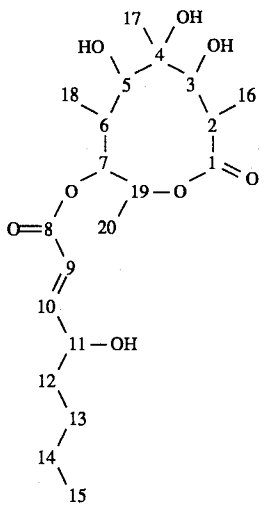

(I)

Botcinolide is produced by culture of a novel strain of the fungus *Botrytis cinerea,* designated UK 195, and may be subsequently recovered from the culture medium and purified.

In accordance with this discovery, it is an object of this invention to provide a novel compound, botcinolide, which has phytotoxic activity, and a method for its production.

It is also an object of this invention to provide new compositions including botcinolide for control of plant growth.

Another object of the invention is to provide a compound which may be used as a biodegradable contact herbicide.

Yet another objective is to provide a new microorganism which can produce botcinolide.

Other objects and advantages of this invention will become readily apparent from the ensuing description.

DETAILED DESCRIPTION OF THE INVENTION

The preferred fungus for the production of botcinolide is a strain of *Botrytis cinerea,* designated UK 185. The strain was isolated in biologically pure form from raspberry fruit (*Rubus ideaus*) growing in Watkinsville, Ga., was identified as *Botrytis cinerea* based upon its characteristic morphology and colonial appearance.

The above-mentioned *Botrytis cinerea* strain UK 185 has been deposited under the Budapest Treaty in the Agricultural Research Service Culture Collection in Peoria, Ill., on Apr. 5, 1995, and has been assigned Deposit No. NRRL 21421.

As described by Gilman (A Manual of Soil Fungi, second edition, Iowa State University Press, Ames, Iowa, 1957, pages 298–300), colonies are diffuse, gray, gray-green, dark olive-green to brown-black, seldom brown or reddish-green. Colonies appear dusty from conidia, may be loose or dense, and are up to 2 mm high.

Morphologically, the conidiophores of the fungus are erect, unbranched or seldom branched, septate, 11–23μ thick, with a black-brown wall which is almost hyalin toward the tip, and with several (three or more) projections at the tip from which the conidia are formed singly on very fine warts. The point of the conidiophore grows between the warts, pressing them back, usually some distance from one another, and they become lateral. The conidia stand so thickly on the projections that thick heads are produced which soon fall off. Conidia are ovate or elliptical to almost globose, finely apiculate at the base, 9–12×6.5–10μ, with an almost hyalin, slightly brown wall.

For the purpose of this invention, any isolate of *Botrytis cinerea* having the identifying characteristics of strain UK 185, including subcultures and variants thereof which retain the ability to produce botcinolide, are effective. The term variants is defined herein to include transformants and mutants of *Botrytis cinerea* which are capable of producing botcinolide.

The fungi of this invention may be cultivated by any conventional means under any convenient aerobic conditions that are effective to promote growth and botcinolide production. While botcinolide may be produced by solid-substrate fermentation, optimal production and recovery of the compound is obtained by liquid-substrate fermentation with agitation. A variety of well-known liquid and solid media may be used. Preferred liquid media include but are not limited to Mycological broth, Sabouraud dextrose broth, Brain-heart infusion broth, and particularly Potato dextrose broth. The fungus will grow over wide pH and temperature ranges, with acceptable ranges being about 2–7 and 0°–40° C., respectively, with a pH of about 5.5 and a temperature range between about 25°–30° C. being preferred.

Under these suitable cultivation conditions, the subject fungus will produce botcinolide which may be subsequently recovered from the culture medium and purified. Botcinolide may be recovered from the culture broth by extraction with a suitable nonpolar solvent, preferably ethyl acetate or a polar/nonpolar solvent such as acetone. Removal of the mycelia and cells prior to such solvent extraction is optional. The solvent phase extract may be separated from the solids and aqueous phase, and the solvent subsequently removed, for example, by evaporation to yield a crude extract of botcinolide.

Purification of botcinolide from the crude extract may be effected by use of conventional techniques including, but not limited to, countercurrent distribution, column chromatography, high-performance liquid chromatography, and thin-layer chromatography. Without being limited thereto, the details of the preferred purification procedure are described in Example 1.

Commercial formulations of botcinolide may be prepared directly from crude extracts of the fermentation medium, thereby obviating the need to isolate the compound in pure form. However, for applications requiring a high degree of specificity or predictability of the intended response, it would normally be preferred to prepare the formulations from pure or substantially pure botcinolide. A preparation of pure or substantially pure botcinolide would exclude other extraneous substances in the natural fungi which might have an adverse effect on the intended activity, or have a toxic effect toward non-target species.

The potency of botcinolide dictates that it be applied in conjunction with a suitable solid or liquid inert carrier or vehicle as known in the art. Of particular interest are those which are agronomically acceptable. Alcohols, ketones, esters, and aqueous surfactant mixtures are illustrative of suitable liquid carriers. The compound may also be formulated with solid inert carriers such as talc, clay or vermiculite, or incorporated into conventional controlled release microparticles or microcapsules. Depending on the substrate, target species, mode of application, and type of response desired, the concentration of active ingredient in the final composition may vary considerably, but typically should be at least about 400 ppm. Factors such as phytotoxicity toward the target plant and tolerance of nontarget species can be used by the skilled artisan in determining the optimum level.

Depending on the target species, concentration of agent, and method of application, botcinolide acts as a herbicide by inhibiting or preventing growth, or inducing mortality of the target plant or seed. The compound is administered in an amount effective to induce the desired response as predetermined by routine testing. Where the ultimate response is control of plant growth, and "effective amount" or "herbicidally effective amount" is defined to mean those quantities of agent which will result in a significant inhibition or prevention of growth of a test group as compared to an untreated group. Without being limited thereto, it is envisioned that application rates of 50–75 g or more of botcinolide per acre will be effective. However, the actual effective amount will of course vary with the species of plant, stage of development, the nature of the substrate, the type of vehicle or carrier, the period of treatment, and other related factors.

To be effective, botcinolide can be directly applied to plants or seeds, or the compound can be applied to the locus of, or the vicinity of, the plant or seed to be controlled. Compositions of the compound will typically be applied by spraying, although solid formulations may be applied by dusting.

Botcinolide is effective in controlling growth of a variety of plants. Without being limited thereto, the compound is particularly effective against monocotyledonous plants and some dicotyledonous plants, including grasses, tobacco, beans, wheat and corn.

The following examples are intended only to further illustrate the invention and are not intended to limit the scope of the invention which is defined by the claims.

EXAMPLE 1

Production of botcinolide.

A strain of *Botrytis cinerea* was isolated from a cultivated raspberry fruit (*Rubus ideaus*) growing in Watkinsville, Ga., and was designated strain UK 185. The taxonomic characteristics of the strain were typical of *Botrytis cinerea.* The biologically pure strain was grown on potato-dextrose agar slants at room temperature for about 14 days and then held at 5° C. for storage.

The potato-dextrose agar slants were flooded with sterile distilled water, and the spores and mycelium suspended therein for use as inoculum. The suspension was transferred to 2.8 l Fernbach flasks, each containing 500 ml of potato-dextrose broth, and incubated on a rotary shaker at 23° C. for 12 days.

After completion of the fermentation, the culture medium was extracted twice with ethyl acetate equal in volume to the aqueous phase, and the solvent phase separated from the aqueous phase and solid material by decantation. The solvent phase was then dried over anhydrous sodium sulfate, reduced in volume under vacuum at 50° C., and chromatographed on silica gel 60 (70–230 mesh) in an open glass column (5×19 cm) using stepwise elution of 500 ml each of benzene, t-butyl methyl ether, ethyl acetate, acetone and acetonitrile. Approximately 25 μl from each fraction was dried under nitrogen and assayed for biological activity as described below.

Bioassays of the chromatography fractions were conducted by the etiolated wheat coleoptile bioassay of Hancock et al. (1964, J. Exp. Biol., 15:166–176). The bioassay was prepared by sowing wheat seed (*Triticum aestivum* L. cv. Wakeland) on moist vermiculite in plastic trays which were sealed with aluminum foil and kept in the dark at 22°±1° C. for four days. Ten 4 mm sections were cut from each seedling and placed in test tubes containing 2 ml of phosphate-citrate buffer at pH 5.6 supplemented with 2% sucrose (Nitsch et al., 1956, Plant Physiol., 31:94–111) and the fraction to be tested for 18 hr (Cutler, Proc. 11th Ann. Meeting Plant Growth Reg. Soc. America, 1984, pp. 1–9). Following this incubation, the coleoptile sections were removed, measured and recorded, and the data were statistically analyzed (Kurtz et al., 1965, Technometrics, 7:95–161).

The fractions that inhibited coleoptile growth, namely the t-butyl methyl ether, ethyl acetate, and acetone fractions were bulked together and reduced in volume under vacuum. This material was chromatographed in a $C_{18}$ reverse-phase glass column (PrepPak 500, Waters Associates; 2×17 cm), using stepwise elution with water and acetonitrile at selected concentrations that ranged from 75:25 of water-acetontrile (v/v) to neat acetonitrile, yielding pure botcinolide. An ultraviolet lamp (366 nm) was used to detect the fluorescent and null zones which were individually collected. Again individual fractions were bioassayed by taking 25 μl aliquots, drying them under nitrogen and examining each fraction with etiolated wheat coleoptiles. Biologically active fractions were determined to be tubes 34–38, inclusive, and these were mixed together and evaporated. Botcinolide significantly inhibited coleoptiles at $10^{-3}$ and $10^{-4}$M by 100 and 82% respectively, relative to controls.

EXAMPLE 2

Phytotoxicity.

Botcinolide was tested on greenhouse-grown bean, corn, and tobacco plants in triplicated experiments. Solutions of the metabolite were formulated by dissolving the material from Example 1 in acetone and adding water that contained 0.1% Tween 20 to yield $10^{-2}$, $10^{-3}$, $10^{-4}$M solutions. The final volume of acetone in each case was 10%. Eight-day-old corn plants (*Zea mays* L., cv. Norfolk Market White) were treated by placing 100 μl of each test solution into individual leaf sheaths, there being four plants in each pot. Eight-day-old bean plants (*Phaseolus vulgaris* L. cv., Black Valentine) were treated in the first true leaf stage, and individual solutions were painted onto the leaves, again using four plants per pot. Individual six-week-old tobacco plants (*Nicotiana tabacum* L. cv., Hick's) were also treated by having their leaves painted with the solutions. Controls consisted of plants treated with aqueous 10% acetone and 0.1% Tween 20.

The treated plants were affected within 24 hr. of treatment and this became even more pronounced at 48 hr. Eight-day-old bean plants treated at $10^{-2}$ showed severe necrosis, especially at the leaf margins, and at $10^{-3}$M there were irregular necrotic areas on the leaves 48 hr after treatment when compared to the control plants. Eight-day-old corn plants treated at $10^{-2}$M showed slight interveinal necrosis, leaf tip damage and slight chlorosis at the point of application relative to the controls 48 hr after treatment. Six-week-old tobacco plants exhibited severe necrosis at $10^{-2}$M, lesser necrosis at $10^{-3}$M, and marginal necrosis at $10^{-4}$ after 48 hr.

One week after teating at $10^{-2}$M, the first internodes of the bean plants were severely stunted, while the corn plants had collapsed. The apical leaves of the tobacco plants had not expanded, and there were necrotic lesions on the first true leaves with a $10^{-2}$M treatment.

EXAMPLE 3

Characterization of Botcinolide.

Thin-layer chromatography was done on silica gel 60, F-254 (E. M. Laboratories) plates developed in toluene-ethyl acetate-formic acid, 5:4:1 (v/v). Botcincolide was visualized by spraying the developed plates with anisaldehyde and heating to 100° C. Ultra-violet data were obtained in methanol with a Beckman 35 spectrophotometer. Infrared spectra were obtained with a Beckman IR 4210 instrument equipped with a 4× beam condenser, and samples were prepared as thin films on KBr windows. Electron impact mass spectra were evaluated by a Hewlett-Packard 5985B mass spectrometer, using a direct probe and low-resolution positive-ion fast atom bombardment (FABMS) and recording data by a VG7070EMF. High-resolution FABMS were evaluated by a Kratos MS50 Triple Analyzer, operated at an accelerating potential of 6 kV. The sample was ionized from a matrix of 3-nitrobenzyl alcohol, using argon. NMR spectra were recorded at 400.13 MHz for $^1$H and at 100.63 MHz for $^{13}$C with a Bruker AMX-400 spectrometer. The sample consisted of about 20 mg of botcinolide in 0.5 ml of $CD_3OD$. All spectra were recorded at 25° C., and the chemical shifts are referenced to the residual solvent signals ($^1$H, 3.3 ppm; $^{13}$C, 49.0 ppm, relative to TMS). Nineteen flasks of *Botyris cinerea* yielded about 190 mg of botcinolide, which was an amorphous solid. Thin-layer chromatography gave a distinct deep-blue spot at Rf 0.52–0.59 upon treatment with acidic anisaldehyde and heating. The UV analysis gave $\lambda$ $MeOH_{max}$ 212 (log $\xi$= 4.14), and the IR spectrum had the major bands at $\nu_{max}$ 3410 (OH), 2950, 2930, 2865, 1728 (C═O), 1722 (C═O), 1708 (shoulder), 1455, 1378, 1368 ($CH_3$), 1318, 1195, 1052, 1029, 965, 828, and 798 $cm^{-1}$. Direct probe, electron impact mass spectrometry gave an incomplete fragmentation pattern, with an apparent $M^+$ at m/z 366 and a major fragment at m/z 97. Neither electron impact nor chemical ionization gave a parent ion peak that could be reconciled with either the $^1$H- or $^{13}$C-NMR data. Subsequently, LRFABMS gave $(M+H)^+$ at 403.34 with fragments at 385.33 $(M-H_2O+H)^+$ at 367.33 $(M-2H_2O+H)^+$. The structure was constructed from the FAB data, which gave a molecular formula of $C_{20}H_{34}O_8$, allowing for 4 rings and/or double bonds. The molecular formula of $C_{20}H_{34}O_8$ was confirmed by HRFAB-MS: $(M+H)^+$ m/z 403.2328 for $C_{20}H_{35}O_8$, Δ=0.4 mmu (that is, the "calculated exact mass" for this formula is 403.2332). There followed extensive NMR spectrometry and the $^1$H and $^{13}$C assignments are shown in Table 1. After considering all the spectroscopic data, they are consistent with the structure shown in (I).

TABLE 1

$^1$H- and $^{13}$C-NMR Data for Botcinolide

| C | $^1$H | $^{13}C^a$ |
|---|---|---|
| 1 | | 180.1(s) |
| 2 | 2.74 (dq, 2.3, 7.1) | 39.7(d) |
| 3 | 3.57 (d, 2.3) | 77.6(d) |
| 4 | | 79.9(s) |
| 5 | 3.78 (d, 10.8) | 72.4(d) |
| 6 | 1.87 (m,4.9, ≈10, 10.8) | 39.3(d) |
| 7 | 4.33 (br.t, ≈10, 10.8) | 78.4(d) |
| 8 | | 167.7(s) |
| 9 | 6.04 (dd, 1.6, 15.6) | 120.1(d) |
| 10 | 6.98 (dd, 4.8, 15.6) | 153.6(d) |
| 11 | 4.24 (m) | 71.5(d) |
| 12 | 1.54 (m) | 37.2 (t) |
| 13 | ≅1.4 (m) | 28.6 (t) |
| 14 | ≈1.4 (m) | 23.6 (t) |
| 15 | 0.92 (br.t, 7.1) | 14.3(q) |
| 16 | 1.32 (d, 7.2) | 17.4(q) |
| 17 | 1.23 (s) | 14.9(q) |
| 18 | 0.97 (d, 4.9) | 14.7(q) |
| 19 | 3.60 (m) | 69.3(d) |
| 20 | 0.99 (d, 4.7) | 18.1(q) |

[a] $^{13}$C multiplicities are from the DEPT spectrum

We claim:

1. A substantially pure compound designated botcinolide and having the structure:

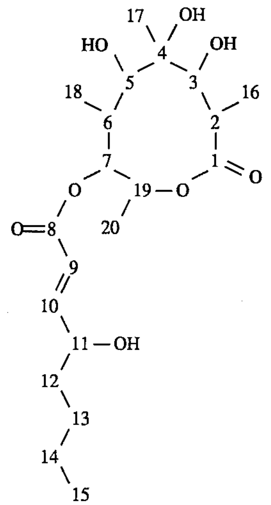

2. A composition comprising a herbicidally effective amount of the compound of claim 1 and an inert carrier.

3. A method for controlling plant growth comprising providing to the locus of a plant or seed a herbicidally effective amount of the compound of claim 1.

4. The method of claim 3 wherein said plant is a monocot.

* * * * *